US00PP32731P2

(12) United States Plant Patent
Capo

(10) Patent No.: US PP32,731 P2
(45) Date of Patent: Jan. 5, 2021

(54) ***PETUNIA* PLANT NAMED 'KLEPH19198'**

(50) Latin Name: *Petunia hybrida*
Varietal Denomination: KLEPH19198

(71) Applicant: Klemm+Sohn GmbH & Co. KG, Stuttgart (DE)

(72) Inventor: Antonella Capo, Latina (IT)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/865,817

(22) Filed: May 4, 2020

(51) Int. Cl.
*A01H 5/02* (2018.01)
*A01H 6/82* (2018.01)

(52) U.S. Cl.
USPC ..... Plt./356.13
CPC ..... *A01H 6/824* (2018.05)

(58) Field of Classification Search
USPC ..... Plt./356.13
CPC ..... A01H 6/824
See application file for complete search history.

(56) References Cited

PUBLICATIONS

UPOV hit on *Petunia* plant named, 'KLEPH19198', QZ PBR 20201051, filed Apr. 21, 2020.*

* cited by examiner

*Primary Examiner* — Anne Marie Grunberg
(74) *Attorney, Agent, or Firm* — Weatherly IP Solutions, LLC; James Weatherly

(57) ABSTRACT

A new *Petunia* plant particularly distinguished by having a brilliant magenta with a well-defined white star along mid-veins of corolla lobes and a semi-trailing plant habit, is disclosed.

1 Drawing Sheet

Genus and species: *Petunia hybrida.*
Variety denomination: 'KLEPH19198'.

BACKGROUND OF THE NEW PLANT

The present invention comprises a new and distinct variety of *Petunia*, botanically known as *Petunia hybrida* and hereinafter referred to by the variety name 'KLEPH19198'. 'KLEPH19198' is a selection from a cross-pollination of the proprietary female *Petunia* line 'PH-2014-0044' (unpatented) and the commercial male *Petunia* line 'Peppy Purple' (unpatented).

In July of 2014, the proprietary female *Petunia* line 'PH-2014-0044' and the proprietary male *Petunia* line 'Peppy Purple' were cross pollinated in Latina, Italy and seeds were obtained. The seeds were sown and plants were grown for evaluation. A plant line was selected in April 2015 in Latina, Italy and named 'KLEPH19198'. In May 2015, 'KLEPH19198' was first vegetatively propagated by terminal tip cuttings and tissue culture in Latina, Italy. 'KLEPH19198' was found to reproduce true to type in successive generations of asexual propagation via tissue culture and terminal tip cuttings.

SUMMARY

The following are the most outstanding and distinguishing characteristics of this new variety when grown under normal horticultural practices in Latina, Italy.

1. Brilliant magenta with a well-defined white star along mid-veins of corolla lobes; and
2. A semi-trailing plant habit.

DESCRIPTION OF THE PHOTOGRAPH

This new *Petunia* plant is illustrated by the accompanying photograph, which shows a close-up of the flower of the plant. The plant is about 11 weeks old grown in Stuttgart, Germany in March 2020. The colors shown are as true as can be reasonably obtained by conventional photographic procedures.

DESCRIPTION OF THE NEW VARIETY

The following detailed descriptions set forth the distinctive characteristics of 'KLEPH19198'. The data which define these characteristics were collected from asexual reproductions carried out in Latina, Italy. Data was collected on fourteen-week-old plants grown indoors in Latina, Italy under greenhouse conditions in March 2020. Color references are to The R.H.S. Colour Chart of The Royal Horticultural Society of London (R.H.S.), 5$^{th}$ edition (2007).

Classification:
- *Family.*—Solanaceae.
- *Species.*—*Petunia hybrida.*
- *Common name.*—*Petunia.*
- *Variety.*—'KLEPH19198'.

Parentage:
- *Female.*—Proprietary *Petunia* line 'PH-2014-0044'.
- *Male.*—Proprietary *Petunia* line 'Peppy Purple'.

Plant:
- *Form and habit.*—Medium vigor plant with semi-trailing habit.
- *Height* (*from top of soil*).—About 15.0 cm.
- *Width* (*horizontal plant diameter*).—About 30.0 cm.
- *Propagation.*—Time to produce a finished flowering plant: 12 to 14 weeks in winter under short day conditions, about 8 weeks in spring. Time to initiate and develop roots: 2 to 3 weeks.

*Root description*.—Moderate density, moderate branching, white roots.

Stems:

*Average number* (*basal*).—About 5.

*Length of basal branches* (*from the base of the stem to the tip*).—Up to 15.0 cm.

*Internode length*.—Up to 2.5 cm.

*Diameter of branches* (*from midpoint*).—About 0.3 cm.

*Stem color*.—RHS 144B.

*Anthocyanin*.—Present at leaf margin RHS N92A.

*Texture*.—Pubescent.

Leaves:

*Arrangement*.—Alternate along the stem, opposite under the inflorescence.

*Length*.—Up to 6.0 cm.

*Width*.—Up to 3.0 cm.

*Shape*.—Elliptic.

*Apex*.—Acute.

*Base*.—Attenuate.

*Margin*.—Entire.

*Immature leaf color*.—Upper surface: RHS N137A. Lower surface: RHS 137C.

*Mature leaf color*.—Upper surface: RHS N137A. Lower surface: RHS 137C.

*Texture*.—Upper surface: Pubescent. Lower surface: Pubescent.

*Venation pattern*.—Arcuate.

*Venation color*.—Upper surface: RHS 144A. Lower surface: RHS 144C.

*Petioles*.—Length: Up to 1.0 cm. Diameter: About 0.3 cm. Color: RHS 144B. Texture: Pubescent.

Flower bud:

*Shape*.—Irregularly oblong.

*Length*.—About 3.5 cm.

*Diameter*.—0.8 cm.

*Color at tight bud*.—RHS 145B along the body of the bud and RHS 79B toward the tip.

*Texture*.—Slightly pubescent.

Inflorescence:

*Blooming habit* (*flowering season*).—Continuously flowering during spring and summertime.

*Inflorescence type*.—Sympodial, with monochasial growth.

*Number of flowers per node*.—1.

*Lastingness of individual blooms on the plant*.—About 12 days.

*Fragrance*.—Not detected.

*Flowers*.—Arrangement: Composed of 5 fused petals. Diameter (flower face): Up to 6.0 cm. Depth (total length of flower): Up to 5.5 cm. Throat/Funnel: Length: About 2.3 cm. Diameter (at opening): About 1.0 cm. Texture: Inner surface: Smooth. Outer surface: Pubescent. Color: Inner surface: RHS NN155B. Outer surface: RHS 157B. Petals: Color, mature flower (fully opened): Upper surface: RHS most similar N78A and RHS 69D along mid-veins of corolla lobes. Lower surface: RHS 72B and RHS N155B along mid-veins of corolla lobes. Apex: Truncate. Base: Fused. Shape: Salverform. Margin: Entire. Strength of waviness: Absent or very weak. Degree of lobation: Medium.

*Calyx arrangement*.—Composed of 5 sepals fused at the base.

*Sepals*.—Color: Upper surface: RHS 137B. Lower surface: RHS 137C and RHS N92A toward the base. Length: Up to 2.5 cm. Width: Up to 0.6 cm. Shape: Oblong. Apex: Acute. Base: Attenuate. Margin: Entire. Texture: Upper surface: Pubescent. Lower surface: Pubescent.

*Pedicels*.—Color: RHS 144A. Length: Up to 4.5 cm. Diameter: About 0.15 cm. Texture: Pubescent.

Reproductive organs:

*Stamens*.—Quantity: 5. Shape: Needle with oblong head. Filament: Length: Up to 1.1 cm. Diameter: About 0.05 cm. Color: RHS N155D. Anther: Shape: Oblong. Color: RHS 10C. Length: about 0.2 cm. Diameter: About 0.15 cm. Pollen: Color: RHS 158A. Amount: Sparse.

*Pistils*.—Quantity per flower: 1. Length: About 2.2 cm. Stigma color: RHS 157C. Style color: RHS 145A.

Fruit and seed set: None observed.

Disease and pest/insect resistance: None observed.

COMPARISON WITH PARENTAL LINES AND KNOWN VARIETY

'KLEPH19198' is a distinct variety of *Petunia*. 'KLEPH19198' is distinguished from its parents as described in Table 1:

TABLE 1

Comparison with Parental Lines

| Trait | Variety 'KLEPH19198' | Female parent 'PH-2014-0044' | Male Parent 'Peppy Purple' |
|---|---|---|---|
| Flower color | Brilliant magenta with a well defined white star along mid-veins of corolla lobes | Magenta purple with unregular yellow zones | Purple and white bicolor |
| Plant habit | Semi trailing | Semi-trailing | Upright |

'KLEPH19198' is most similar to the commercial *Petunia* plant named 'Peppy Purple' (unpatented). Differences between the two varieties are described in Table 2:

TABLE 2

Comparison with Similar Variety

| Characteristic | Variety 'KLEPH19198' | Commercial line 'Peppy Purple' |
|---|---|---|
| Plant habit | Semi trailing | Upright |
| Color pattern | Very stable white star along mid-vein of corolla lobes | Color distribution variable and playing in different environmental conditions |

I claim:

1. A new and distinct variety of *Petunia* plant named 'KLEPH19198' as illustrated and described herein.

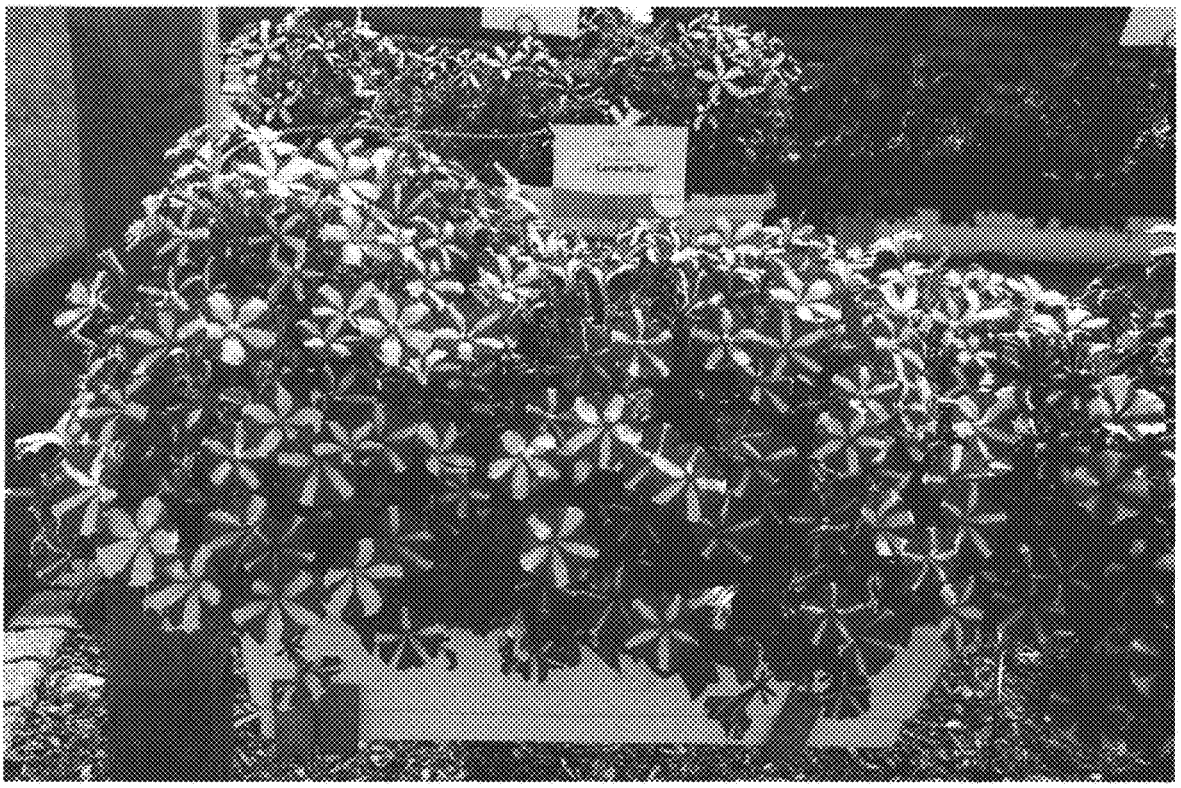

* * * * *